United States Patent [19]

Campbell et al.

[11] Patent Number: 5,800,522
[45] Date of Patent: Sep. 1, 1998

[54] INTERIOR LINER FOR TUBES, PIPES AND BLOOD CONDUITS

[75] Inventors: Carey V. Campbell; James F. Kasic, II; Larry J. Kovach; Alvaro J. Laguna; James D. Lewis; Mark E. Mayrand, all of Flagstaff; David J. Myers, Camp Verde; Stanislaw L. Zukowski, Flagstaff, all of Ariz.

[73] Assignee: W. L. Gore & Associates, Inc., Newark, Del.

[21] Appl. No.: 789,378

[22] Filed: Jan. 24, 1997

Related U.S. Application Data

[63] Continuation-in-part of Ser. No. 499,423, Jul. 7, 1995.

[51] Int. Cl.$^6$ .................................................. A61F 2/06
[52] U.S. Cl. ............................................................ 623/1
[58] Field of Search ................................ 623/1, 11, 12

[56] References Cited

U.S. PATENT DOCUMENTS

| | | |
|---|---|---|
| 3,953,566 | 4/1976 | Gore. |
| 4,177,334 | 12/1979 | Okita. |
| 4,187,390 | 2/1980 | Gore. |
| 4,197,880 | 4/1980 | Cordia. |
| 4,355,664 | 10/1982 | Cook et al. |
| 4,791,966 | 12/1988 | Eilentropp. |
| 4,925,710 | 5/1990 | Buck et al. |
| 5,122,154 | 6/1992 | Rhodes. |
| 5,123,917 | 6/1992 | Lee. |
| 5,152,782 | 10/1992 | Kowligi et al. |
| 5,500,014 | 3/1996 | Quijano .......... 623/2 |
| 5,607,445 | 3/1997 | Summers. |
| 5,609,598 | 3/1997 | Laufer ............ 623/2 |
| 5,609,626 | 3/1997 | Quijano .......... 623/1 |

FOREIGN PATENT DOCUMENTS

| | | |
|---|---|---|
| 9505131 | 2/1995 | WIPO. |
| 9505277 | 2/1995 | WIPO. |
| 9505555 | 2/1995 | WIPO. |
| 9600103 | 1/1996 | WIPO. |
| 9633066 | 10/1996 | WIPO. |

OTHER PUBLICATIONS

Rosenfeld J C et al. Endothelial Infiltration and Lining Of Knitted Dacron Arterial Grafts. Surgical Forum 1981; 132:336–38.

Onuki Y et al. Accelerated Endothelialization Model For The Study Of Dacron Graft Healing. Annals of Vascular Surgery 1997; 11:141–48.

Graham L M et al. Enhanced Endothelialization of Dacron Grafts By External Vein Wrapping. Journal of Surgical Research 1995; 38:537–45.

(List continued on next page.)

*Primary Examiner*—Michael J. Milano
*Attorney, Agent, or Firm*—Wayne D. House

[57] ABSTRACT

A tube which circumferentially distends from its initial circumference upon the application of a circumferentially distending force such as applied by an internal pressure, and which exhibits minimal recoil following the removal of the circumferentially distending force. The tube preferably has a second circumference larger than the initial circumference which remains substantially unchanged by further increasing force once it has been achieved. Because of the distensible circumference and minimal recoil of the tube, the tube is useful as a liner for pipes and vessels and particularly for pipes and vessels having irregular internal surfaces to which the tube can smoothly conform. The tube is preferably made from porous PTFE with thin walls, in which form it is particularly useful as a liner for both living and prosthetic blood vessels and to line anastomoses between living and prosthetic blood vessels. The tube or any other intraluminal graft may be used in in situ bypass procedures to hold venous valves open and to occlude tributary branches. Covered stents may be used for the same purpose; stents without such a covering may also be used to hold venous valves open.

29 Claims, 6 Drawing Sheets

OTHER PUBLICATIONS

Bull D A et al. Cellular Origin and Ratoe of Endothelial Cell Coverage of PTFE Grafts. Journal of Surgical Research 1995; 58:58–65.

Sterpetti A V. Healing of High–Porosity Polytetrafluoroethylene Arterial Grafts Is Influenced By The Nature Of The Surrounding Tissue. Surgery 1992; 111:667–82.

Lepidi S. The Degree of Porosity Influences The Release of Growth Factors By Healing Polytetrafluoroethylene (PTFE) Grafts. Eur Journal of Vascular and Endovascular Surgery 1996; 11:36–41.

Sedlairk K M et al. Rapid Endothelialization of Microporous Vascular Prostheses Covered With Meshed Vascular Tissue: A Preliminary Report. Biomaterials 1990; 11:4–7.

Holubec H et al. the Relationship Between PTFE Graft Ultrastructure and Cellular Ingrowth: The Influence Of An Autologous Jugular Vein Wrap. Biomaterials Mechanical Properties 1994; 53–64.

Ahn SS et al. Endovascular Femoropopliteal Bypass: Early Human Cadaver and Animal Studies. Ann Vasc Surg 1995;9:28–36.

Dake MD et al. Transluminal Placement of Endovascular Stent–Graftrs For The Treatment of Descending Thoracic Aortic Aneurysms. New England J Medicine 1994;331:1729–34.

Marin ML et al. Transluminally placed endovascular stented graft repair for arterial trauma. J Vasc Surg 1994;20:466–73.

Parodi JC. Endovascular repair of abdominal aortic aneurysms and other arterial lesions. J Vasc Surg 1995;21:549–57.

INTERIOR LINER FOR TUBES, PIPES AND BLOOD CONDUITS

RELATED APPLICATIONS

The present application is a Continuation-in-Part of copending U.S. patent application Ser. No. 08/499,423 filed Jul. 7, 1995.

FIELD OF INVENTION

This invention relates to the field of interior liners for pipes and tubes and particularly to liners for blood conduits.

BACKGROUND OF THE INVENTION

There exists a need for a liner to provide a new interior surface lining for pipes and tubes in various applications. A liner having a smaller circumference than the inner circumference of the tube or pipe intended to be lined could be easily located axially within that pipe or tube. If such a liner were circumferentially distensible by the application of an internal pressure it could be expected to conform to the topography of the inner surface of the pipe or tube during use even if that surface were rough and irregular. Alternatively, an inflatable balloon could be used to circumferentially distend the liner to cause it to conform to the interior surfaces of the tube being lined. The ends of the liner could be affixed to the interior surface of the lined pipe or tube by various known mechanical fastening means; in some instances it may not require fastening, particularly at the downstream end. Such a liner would be of even greater utility if it were made from a highly chemically inert material.

Particularly useful applications of such a concept would be as an interior liner for prosthetic vascular grafts or natural vessels. For example, the liner could be installed within arteriovenous grafts cannulated by dialysis needles for kidney dialysis. Such grafts presently have a useful life expectancy often limited by the number of times they can be cannulated due to damage caused to the graft wall by the needles. Repeated cannulation in the same region results in fluid leakage through the graft. Once excessive leakage occurs, the graft is abandoned or bypassed. If it were possible to extend the life of the graft by providing it with a new interior lining surface, the graft could continue to be used for cannulation by dialysis needles and the patient would be spared the additional trauma and disfigurement resulting from implanting an entirely new graft. Such a liner may also inhibit tissue growth that often leads to unacceptable narrowing of the flow cross section. It might be useful for providing a smoother flow surface for anastomoses of vascular grafts or living blood vessels including graft-to-blood vessel anastomoses. The liner could also be used to provide additional strength to weak or damaged blood vessels or vascular grafts, or to intentionally occlude side tributaries in living blood vessels. Further, the inner surfaces of diseased vessels could be lined subsequent to enlarging the flow channel via balloon angioplasty, thrombectomy, or by other means.

Various published documents describe the use of porous PTFE vascular grafts as interior liners for blood conduits. See, for example, Marin M L et al., "Transluminally placed endovascular stented graft repair for arterial trauma," J Vasc Surg 1994; 20:466–73; Parodi J C, "Endovascular repair of abdominal aortic aneurysms and other arterial lesions," J Vasc Surg 1995; 21:549–57 and Dake M D et al., "Transluminal placement of endovascular stent-grafts for the treatment of descending thoracic aortic aneurysms," New England Journal of Medicine 1994; 331:1729–34. U.S. Pat. Nos. 5,122,154 to Rhodes and 5,123,917 to Lee describe similar applications. These documents typically describe the use of GORE-TEX® Vascular Grafts or Impra® Grafts as intraluminal grafts or interior liners for blood conduits. These commercially available porous PTFE vascular Grafts have specific disadvantages as interior liners.

GORE-TEX Vascular Grafts are porous PTFE tubes having a helical wrap of a reinforcing film that substantially prevents circumferential distension. The Impra Grafts do not have such a reinforcement and so may be circumferentially distended, however, these grafts will recoil significantly on release of the distending force and therefore must be retained in place by the use of mechanical means such as balloon expandable metal stents. Also as a result of the lack of a reinforcing layer, these grafts continue to circumferentially distend with exposure to increasing pressure and so do not have a second circumference at which the circumference stabilizes and does not substantially further distend with increasing pressure.

The disadvantages of presently available vascular graft materials for use as intraluminal grafts are well documented. For example, in a paper entitled "Endovascular Femoropopliteal Bypass: early Human Cadaver and Animal Studies" (Ann Vasc Surg 1995;9:28–36), Doctor Ahn writes in describing the effectiveness of presently available intraluminal graft materials, "However, before this idea can be translated to broad clinical use, multiple problems still need to be resolved and/or avoided. The current study clearly shows the importance of a proper size match between the graft and the artery." There is clearly a need for more effective intraluminal graft materials that are circumferentially distensible in order to conform smoothly to vessel walls without allowing retrograde dissection due to substantial recoiling of the graft following circumferential distension.

SUMMARY OF THE INVENTION

The present invention is an interior liner for tubes, pipes and blood conduits comprising a tubular form circumferentially distensible and conformable whereby the first circumference of the interior liner (the initial circumference of the liner at zero pressure) may be distended by the application of pressure causing the first circumference to be increased to a larger circumference. The qualities of being circumferentially distensible under pressure and conformable allow the interior liner to be placed into another pipe or tube and be circumferentially distended under pressure until the interior liner is smoothly conforming without gross wrinkles to the interior surface of the other pipe or tube even if that surface represents a rough, irregular, damaged or otherwise non-uniform topography. The use of a porous polymer to construct the interior liner enhances its ability to conform.

For applications in which the pipe, tube, or blood conduit to be lined may not have adequate strength to resist expected normal fluid operating pressures, the interior liner of the present invention is preferably provided with a self-limiting circumference whereby it is circumferentially distensible up to a second circumference beyond which it will not substantially distend if used within the designed range of operating pressures. Pressures approaching the burst pressure of the interior liner are necessary to cause further substantial circumferential distension beyond the second circumference. The circumference can, however, be expected to grow in response to creep (time-dependent plastic deformation). This self-limiting feature is useful for lining weakened pipes, tubes or blood conduits whereby the liner itself is capable of withstanding the normal fluid operating pressure of the lined system.

Blood conduits include living blood vessels (veins and arteries) and vascular grafts of both prosthetic and natural materials. Vascular grafts of natural materials include, for example, materials of human umbilical components and materials of bovine origin.

In another embodiment, the interior liner of the present invention has minimal recoil after being circumferentially distended so that it remains proximate with all interior surfaces of the pipe, tube or blood conduit to which it has been fitted. Minimal recoil is considered to mean recoiling diametrically (or circumferentially) in an amount of 14 percent or less and more preferably 10 percent or less from a diameter to which the liner has been circumferentially distended by an amount of 25 percent, with the recoiled diameter measured 30 minutes following the release of the circumferentially distending force.

Particularly for applications relating to use as a liner for blood conduits, it is preferred that the interior liner have a second circumference beyond which it is not readily distensible and minimal recoil. For many of these applications, it may also be preferred that the liner have a wall thickness of 0.25 mm or less.

The term circumference is used herein to describe the external boundary of a transverse cross section of the article of the present invention. For any given amount of distension, the circumference is the same whether the article is wrinkled, folded or smooth.

Intraluminal grafts and particularly the intraluminal graft or liner of the present invention may be used for in situ vascular bypass grafting as a means of holding open the leaflets of venous valves within a vein segment being used for the bypass. The various side branch vessels or tributaries of the vein segment may also be occluded by the intraluminal graft. Stents provided with a covering of graft material may be also be used for this same application. Likewise, conventional stents (having perforations through their tubular walls) may also be used to hold the venous valves in a permanently open position although the presence of perforations through their tubular walls prevents their use for occluding tributary vessels.

DETAILED DESCRIPTION OF THE INVENTION

The interior liner of the present invention is preferably made from porous PTFE and most preferably porous PTFE having a microstructure of nodes interconnected by fibrils made as taught by U.S. Pat. Nos. 3,953,566 and 4,187,390, both of which are herein incorporated by reference. When comprised of porous PTFE, the interior liner has additional utility because of the chemically inert character of PTFE and has particular utility as a liner of blood conduits including living arteries and veins, vascular grafts and various repairs to blood conduits, particularly including the lining of anastomoses. The porosity of the porous PTFE can be such that the interior liner is substantially impervious to leakage of blood and consequently does not require preclotting. For use as a blood conduit liner, the interior liner may preferably have a very thin wall thickness such as in the range of 0.10 to 0.25 mm and may be made to be even thinner; U.S. Pat. No. 4,250,138 describes a method of manufacturing porous PTFE tubes having such very thin wall thicknesses. Alternatively, the interior liner can be made to have wall thicknesses of greater than 0.25 mm if that were to be desirable for some applications.

The interior liner is preferably made to have a second circumference beyond which the circumference of the liner will not distend significantly unless the normal system operating pressure is substantially exceeded. For example, in the case of an interior liner intended for use as a blood conduit liner, pressures in excess of twenty-five times normal human systolic blood pressure (120 mm Hg) may be required to cause the interior liner of the present invention to substantially increase in circumference beyond its second circumference. One embodiment of the blood conduit interior liner would, for example, have an initial inside diameter of about 3.5 mm prior to circumferential distension. This small initial diameter allows for easy insertion into blood conduits. The second circumference of this embodiment would correspond to a diameter of, for example, 8 mm, so that the liner would be most useful for lining blood conduits having inside diameters of up to about 8 mm. The second circumference for this embodiment, corresponding to a diameter of 8 mm, prevents further distension of the circumference of the blood conduit under virtually all normal operating conditions. The second circumference is established by the presence of a thin film tube of helically wrapped porous PTFE film. The film tube can be bonded to the outer surface of a substrate tube of porous PTFE. This substrate tube is preferably made by longitudinal extrusion and expansion whereby a seamless tube is created; alternatively, the substrate tube may be made from a layer of porous PTFE film oriented substantially parallel to the longitudinal axis of the tube and having a seam in this same direction. The helically wrapped porous PTFE film is comprised primarily of fibrils which are oriented in a substantially circumferential direction around the outer surface of the substrate tube thereby restraining and limiting the second circumference of the resulting interior liner. The helically wrapped porous PTFE film is preferably wrapped in opposing directions with respect to the longitudinal axis of the tube. Such an interior liner may also be made from helically wrapped porous PTFE film wrapped helically in opposing directions without the use of a substrate tube.

Conversely, the interior liner may be made so as not to have a second circumference for applications not requiring additional circumferential strength.

The resistance of the interior to circumferential distension by pressure can be varied. For example, an interior liner can be made having a very thin wall thickness in order to be capable of being distended by blood pressure alone which may allow for relatively simple installation of the liner. Alternatively, the interior liner may be made to require a greater distending force to cause it to conform to the interior surface of a blood conduit, such as a distending force supplied by the inflation of a balloon catheter. Such balloon catheters are used conventionally to increase the diameter of balloon expandable metal stents during implantation of such stents into blood conduits as well as to increase the flow cross section in partially occluded living blood vessels. An interior liner requiring such a higher distending force is the result of the use of a substrate tube having a greater wall thickness, the use of more helically wrapped film around the exterior surface of the substrate tube, or both.

Previously available porous PTFE tubes that allow any appreciable amount of circumferential distensibility under pressure also recoil significantly when the pressure is removed and so require mechanical support such as stents along their entire length to hold them against the interior surface of a blood conduit. For most blood conduit applications it is preferable that the liner not recoil. Various embodiments of the present invention provide an interior liner that allows substantial circumferential distensibility without appreciable recoil which in turn allows for relatively easy insertion and deployment into a blood conduit, maximizes available cross sectional flow area by conforming uniformly to the interior surface of the blood conduit, and minimizes fluid accumulation between the liner and the blood conduit.

The percentage recoil of an interior liner is determined with the use of a tapered metal mandrel having a smooth, polished exterior surface. A suitable taper is 1.5 degrees from the longitudinal axis. Preferably the mandrel is provided with incremental diameter graduations at intervals whereby the inside diameter of a tube may be determined by gently sliding a tube onto the smaller diameter end of the mandrel and allowing the tube to come to rest against the tapered mandrel surface and reading the appropriate graduation. Alternatively the inside diameter of the tube may be measured by viewing the tube and mandrel, fitted together as previously described, using a profile projector measurement system. Using either a graduated mandrel or a profile projector, percentage recoil of an interior liner is determined by first measuring the initial diameter of the liner. The liner is then gently slid further onto the tapered mandrel with a minimum of force until a diameter increase of 25% is obtained. This increased diameter is considered to be the distended diameter. The liner is then pushed from the mandrel, avoiding the application of tension to the liner. After waiting at least 30 minutes to allow the liner to recoil, the recoil diameter is determined using the tapered mandrel by performing the same procedure as used to measure the initial diameter. Percentage recoil is then determined using the formula:

$$\frac{\text{Distended diameter} - \text{recoil diameter}}{\text{Distended diameter}} \times 100 = \% \text{ recoil}$$

Minimal recoil is considered to be 14 percent or less and more preferably 10 percent or less.

In one embodiment of the present invention, circumferential distension results in some degree of twisting along the length of the liner. For applications requiring maximum conformability to irregular surface topography, alternative embodiments are described which do not twist along their length during circumferential distension.

The conformability and distensibility of the interior liner allow it to effectively line blood conduits even when the interior topography is irregular and non-uniform. Relatively tortuous blood conduits, acutely curved conduits and tapered conduits may be provided with a relatively smooth lining. The blood conduit liner having a second circumference is anticipated to be useful to repair aneurysms including aortic aneurysms and otherwise weak blood conduits. The interior liner is expected to be generally useful to provide a new flow surface to previously stenosed vessels, particularly in veins anastomosed to arteriovenous vascular grafts and in peripheral vessels such as those in the legs. It is also expected to be useful for the repair of arteriovenous access vascular grafts that have been cannulated by dialysis needles to the extent that their further use is jeopardized. The conformable quality of the inventive interior liner can provide such vascular grafts with a new blood flow surface and thereby allow their continued use. The conformability of the liner also allows it to provide a new, smoother flow surface for anastomoses and other blood conduit dissections and may consequently reduce the risk of intimal hyperplasia at the distal end of the graft. The interior liner may be installed without any distal anastomosis thereby reducing the risk of anastomotic hyperplasia. The liner may also be used to occlude side vessels if desired, such as for the conversion of veins to arteries during in situ bypass procedures. The liner may be useful in such procedures to smooth the remnants of removed venous valves or even to hold venous valves open and thereby obviate the need to remove them at all.

The interior liner may be provided in bifurcated or Y-graft configurations to allow lining of, for example, branched blood conduits. The tubular liner may also be cut into sheets if a sheet material such as an implantable repair patch is needed that requires distensibility or conformability.

The interior liner may be manufactured to include a radiopaque substance if it is desired to visualize the liner after implantation into a living body. Such radiopaque substances are well known to those skilled in the art of manufacturing various medical devices such as indwelling catheters.

The interior liner may also be made in diametrically tapered embodiments wherein one end of the liner is made to have a smaller second circumference than the opposite end. As the liner is made according to procedures involving the use of steel mandrels, tapered embodiments may be manufactured by the use of diametrically tapered steel mandrels.

In one embodiment the interior liner can, alternatively, be used as an external covering for tubes, pipes and blood conduits. According to this embodiment the liner is particularly useful as an exterior covering for weakened blood conduits wherein after being fitted coaxially over such a conduit, tension is applied to the opposite ends of the liner thereby causing its circumference to reduce and causing it to conform to the exterior topography of the blood conduit. After tensioning, the ends of the liner are secured to the conduit to prevent dilatation.

The liner may be implanted using conventional surgical techniques. Alternatively, using a catheter introducer, the interior liner is inserted into the vascular system and delivered via a guide wire to the intended location, which may be a location remote from the point of insertion. It may be circumferentially distended at the intended location using a balloon catheter or blood pressure according to the design of the liner. The proximal end may be anchored using a stent, a tissue adhesive or may also be secured if desired by sutures. The distal end may be secured by the same methods, however, the conformability and lack of recoil may allow the liner to be used in many applications without being additionally secured at the distal end.

Figure 5:
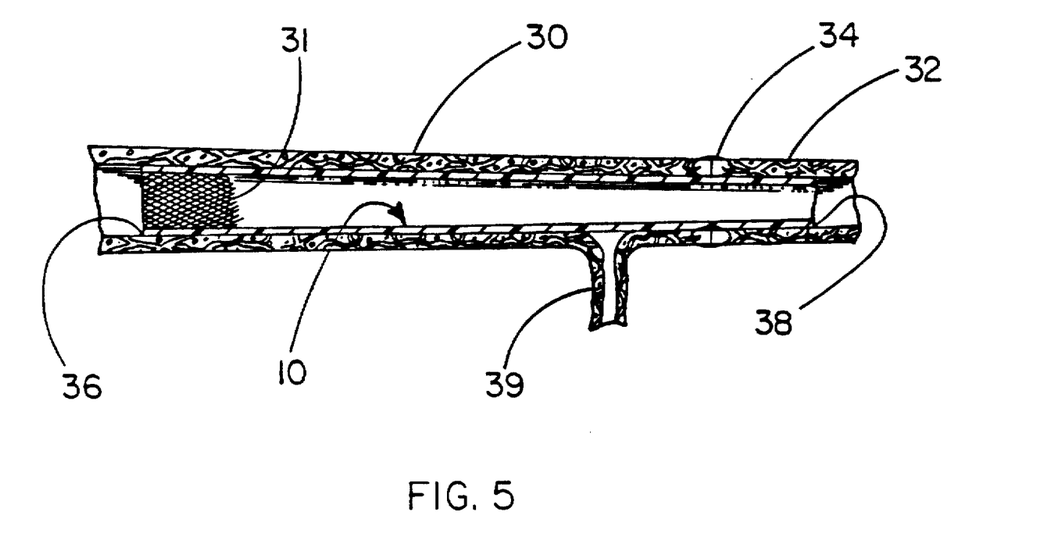
FIG. 5 describes an interior liner secured to a blood conduit by an expandable stent.

FIG. 5 depicts a cross section showing the interior liner 10 in use as a liner for a blood conduit 30 with the proximal end 36 of the liner 10 secured by a stent 31. Distal end 38 remains unsecured. The liner 10 may be used to provide a lining over an anastomosis 34 between adjacent blood conduits 30 and 32; liner 10 may also be used to occlude side vessels 39.

Figure 6:
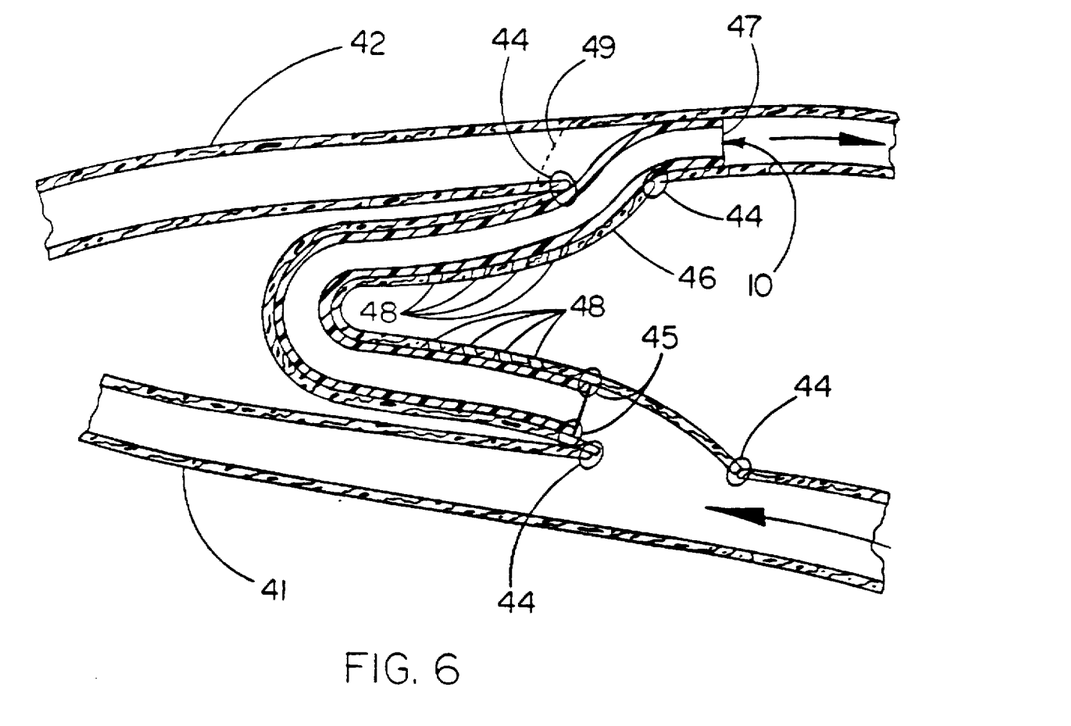
FIG. 6 describes a cross section of an interior liner of the present invention used in the repair of an arteriovenous vascular graft.

FIG. 6 depicts a cross section showing the interior liner 10 used to repair an arteriovenous vascular graft 46. Graft 46 is anastomosed to artery 41 and vein 42 by sutures 44. The arterial end of the liner 10 is secured to the arteriovenous graft 46 by sutures 45. The venous end 47 of the liner 10 may be left without direct mechanical attachment such as by sutures. Vein 42 may be ligated if desired at site 49 adjacent to the anastomosis of the vein 42 and arteriovenous graft 46. Liner 10 covers old cannulation sites 48.

The interior liner is also anticipated to be useful for various industrial and other non-medical applications. Many pipes or tubes having damaged, repaired or otherwise irregular interior or exterior surfaces may benefit from such a liner. Corroded pipes or tubes, especially those conveying chemically reactive fluids, may benefit from the distensible, conformable and inert qualities of the interior liner of the present invention.

Figures 1, 2:
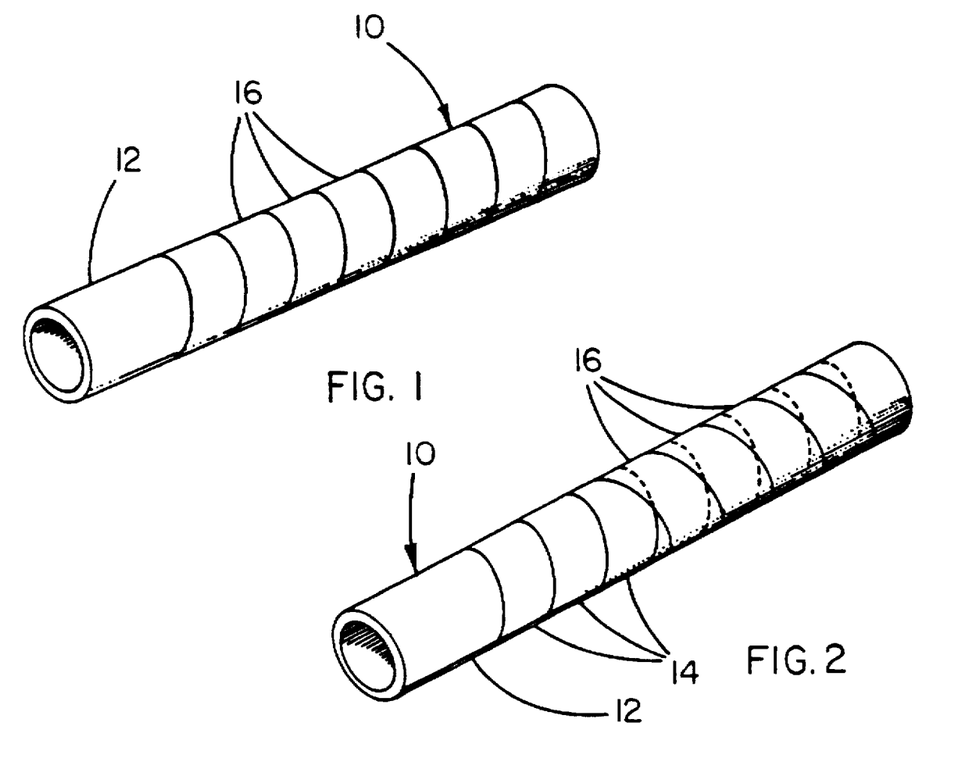
FIG. 1 describes a perspective view of the construction of an interior liner according to the present invention having a layer of helically-wrapped porous PTFE film applied in a single direction over the outer surface of a longitudinally extruded and expanded porous PTFE tube.
FIG. 2 describes a perspective view of the construction of an interior liner according to the present invention having two layers of helically-wrapped porous PTFE film applied in opposing directions over the outer surface of a longitudinally extruded and expanded porous PTFE tube.
Figure 3:
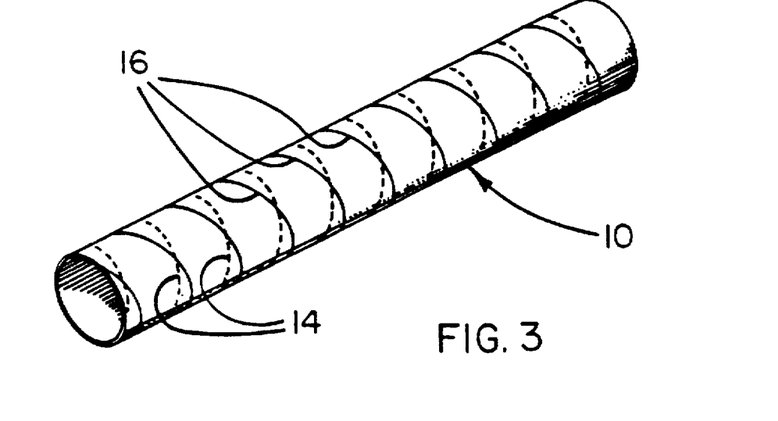
FIG. 3 describes a perspective view of the construction of an interior liner according to the present invention having two layers of helically-wrapped porous PTFE film applied in opposing directions. No separate substrate porous PTFE tube is used beneath the film.

The interior liner 10 described by FIG. 1 comprises a longitudinally extruded and expanded porous PTFE tube 12 having a helical wrapping 16 of porous PTFE film. While this construction is similar in appearance to commercially available GORE-TEX Vascular Grafts, the method of making the liner provides it with circumferential distensibility that is not available in GORE-TEX Vascular Grafts. FIG. 2 describes a more preferred alternative having layers 14 and 16 of helically-wrapped porous PTFE film applied in opposing directions. This embodiment does not twist longitudinally during circumferential distension as can the embodiment of FIG. 1. FIG. 3 describes a perspective view of an interior liner comprising layers 14 and 16 of helically-wrapped porous PTFE film preferably wrapped in two opposing directions. No longitudinally extruded and expanded porous PTFE tube is used beneath the film. According to still another alternative, the interior liner comprises a longitudinally extruded and expanded tube of porous PTFE made without an exterior helical wrapping of film whereby the tube has minimal recoil following release of a circumferentially distending force. This minimal recoil behavior is entirely different from previously available porous PTFE vascular grafts made without exterior film which exhibit significant recoil. This alternative, without the exterior helical wrap of film, is described by the longitudinally extruded and expanded tube 12 portion of FIG. 1.

A preferred process for making the interior liner of the present invention is shown by the flow chart of FIG. 4; the various steps shown by this flow chart are sequentially described as follows according to the number indicated within parentheses for each step. According to step 1, a longitudinally extruded and expanded porous PTFE tube is obtained and fitted coaxially over a stainless steel mandrel having an outside diameter the same as or slightly larger than the inside diameter of the porous PTFE tube. Per step 2, a film tube is made of porous PTFE film by helically wrapping multiple layers of the film in opposing directions onto the surface of another stainless steel mandrel of larger diameter than the previously described mandrel. Step 3 describes heating to bond the overlapping layers together to create a film tube. After allowing the mandrel and film tube to cool to about room temperature, step 4 describes removing the film tube from the mandrel. The inside diameter of the film tube should be substantially larger than the outside diameter of the porous PTFE tube. According to step 5, the film tube is then fitted coaxially over the porous PTFE tube and mandrel and tensioned longitudinally until its inside diameter reduces to the extent that it conforms smoothly to the outer surface of the porous PTFE tube. The ends of the resulting combination film tube and longitudinally expanded and extruded porous PTFE tube are then secured to the mandrel in order to longitudinally restrain them against shrinkage during subsequent heating. As described by step 6, adequate heat is applied to cause the film tube to bond to the porous PTFE tube, after which the composite tube is removed from the mandrel as shown by step 7. According to step 8, the composite tube is fitted over another mandrel of larger diameter but smaller than or equal to the original inner diameter of the film tube. Per step 9, the composite tube and mandrel are then heat-treated for a relatively short time which results in the interior liner having even less recoil after the removal of a circumferential distending force, as long as the distension is to a circumference less than that of the circumference of the mandrel of step 8. Finally, after cooling and removal from this mandrel as described for step 10, per step 11 the liner is again fitted onto a smaller mandrel of the same approximate outside diameter as the original inside diameter of the longitudinally extruded and expanded porous PTFE tube and tensioned longitudinally to cause it to reduce in diameter and conform to the surface of this smaller mandrel. Optionally, as shown by step 12, the liner is longitudinally restrained to the mandrel, following which the liner and mandrel assembly is heat treated to provide it with dimensional stability should it be subsequently exposed to additional heat such as from steam sterilization. After cooling and subsequent removal from the smaller mandrel according to step 13, the interior liner is available for use as a liner of tubes, pipes or blood conduits. The mandrel of step 11 need not be used, in which case the composite tube must be longitudinally restrained by other means in step 12. The small diameter enables it to be easily located axially within the vessel it is intended to line prior to being circumferentially distended.

The graft of the present invention is also anticipated to be particularly useful for in situ vascular bypass grafting procedures in which a vein is transected at the desired locations (thereby creating a vein segment) and reconnected into the arterial system, whereby the vein segment becomes an effective arterial bypass (e.g., in situ bypass grafting procedures wherein the vein segment is left in its original location). The saphenous vein is most typically used. The venous valves must be disrupted or rendered incompetent to prevent interference with arterial flow; likewise, all tributaries of the vein must be ligated or otherwise occluded so that the vein segment is entirely isolated from the venous system for use in its new arterial function. Venous valve disruption typically entails a valvulotomy wherein a valvulotome (a valve disrupting instrument) is inserted distally and advanced proximally through the entire length of the venous segment and then withdrawn, ideally disrupting the valve leaflets during withdrawal. The procedure is problematical due to the unreliability of the valvulotome in that it does not always entirely remove each valve, requiring that the procedure be repeated or risk leaving behind remnants of valve leaflets to accumulate thrombus. Likewise, there is attendant risk of damage to the lumen of the vein by the cutting edges of the valvulotome, particularly at tributaries. The side tributaries are typically occluded by individual surgical ligation. They are difficult to locate; most typically the leg must be opened for the entire length of the vein segment in order to assure that all tributaries have been occluded. This level of trauma results in increased time of operation and healing and increased risk of infection. Likewise, ligation of individual tributaries includes risk of omitting one or more tributaries with the attendant possibility of the creation of arterio-venous fistulas.

Circumferentially distensible tubular articles such as intraluminal grafts are anticipated to provide an effective means of holding the leaflets of venous valves open in order to remove interference to arterial flow and likewise to provide an effective means of occluding tributaries. The intraluminal graft of the present invention is believed to be a preferred graft for this purpose; its porous, thin wall is anticipated to enhance biological compatibility for use with in situ procedures in comparison to previously available intraluminal graft materials.

Figure 8A:
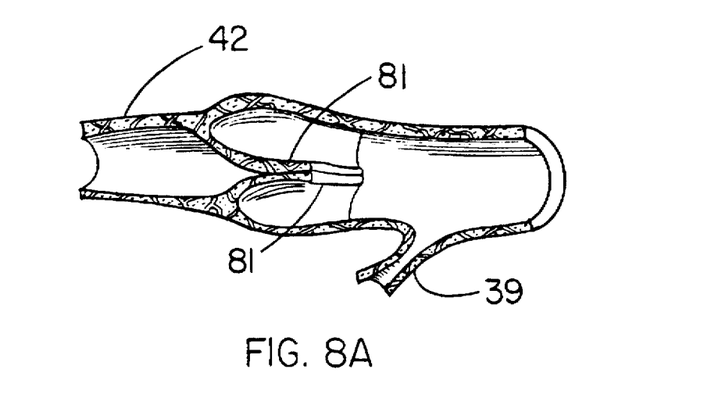
FIGS. 8A–8C are longitudinal cross sections that describe the use of an intraluminal graft to hold a venous valve open and occlude a tributary vessel.

FIG. 8A describes a perspective longitudinal cross section of a vein 42 showing the leaflets 81 of a typical bicuspid venous valve. Tributaries 39 occur at various locations along the length of a typical segment of a saphenous vein normally used for these procedures. A typical length of saphenous vein may include 5-12 tributaries and 2-5 venous valves which all require attention during an in situ procedure. Tributaries frequently occur immediately proximal to a venous valve as suggested by the figure.

Figure 8B:
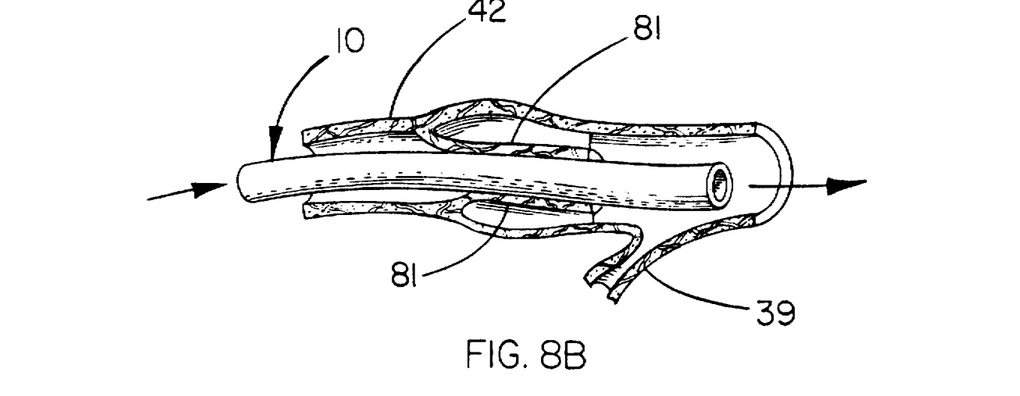
Figure 8C:
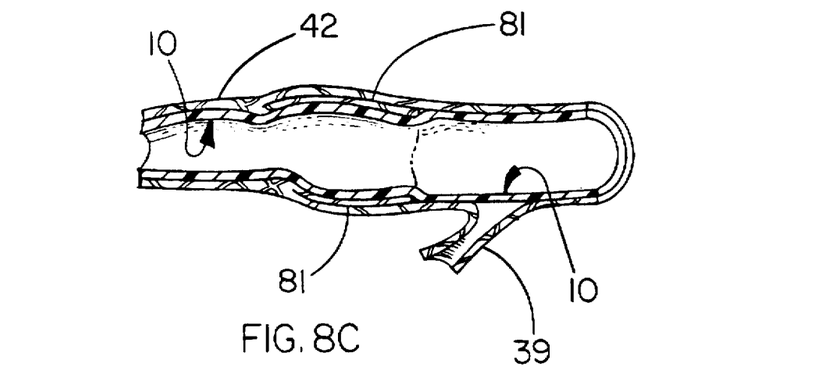

The intraluminal graft of the present invention may be fitted within a vein segment using methods previously described. When inserted into a vein segment and circumferentially distended against the vein wall as shown by FIGS. 8B and 8C, the intraluminal graft effectively holds the leaflets 81 of the venous valve open and also occludes tributaries 39. It accomplishes this in an effective manner without substantial risk of luminal damage to the vein and without the trauma related to individual ligation of tributaries. The risk of significant leaflet remnants remaining in the blood stream is eliminated. It is apparent that the intraluminal graft may be used in a continuous length suitable to line the entire length of the vein segment, occluding all tributaries and holding open all venous valves. Likewise, it is apparent that individual shorter segments of intraluminal graft may be used within the vein segment to individually address venous valves and/or tributaries if desired. Optionally, either or both ends of the intraluminal graft may be secured against the luminal wall of the vein segment by the use of one or more circumferentially distensible stents. If desired, a valvulotomy procedure may be performed to disrupt the valve leaflets prior to inserting the intraluminal graft into the vein segment. The intraluminal graft may also be used to repair damage to vein walls caused during a conventional valvulotomy wherein the graft provides a new luminal surface which covers the damaged regions of the walls.

Figure 9A:
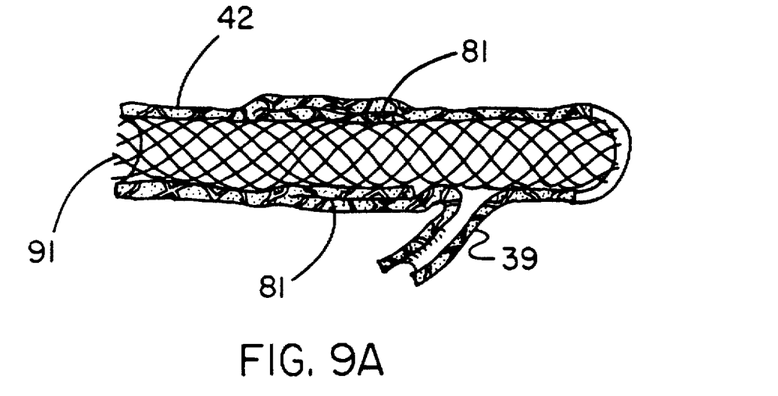
FIG. 9A is a longitudinal cross section that describes the use of a stent to hold open a venous valve.

Alternatively, the circumferentially distensible tubular article may be a circumferentially distensible stent which is inserted into the vein segment and into the venous valve between the opposing leaflets of the valve. As shown by the longitudinal cross section of FIG. 9A, the stent 91 is then circumferentially distended, thereby forcing the leaflets 81 against the luminal surfaces of the vein and holding the leaflets 81 in an open position in order that they cannot substantially interfere with retrograde flow through the vein as they would in a closed position. This use of stents is anticipated to be of particular utility in in situ bypass applications wherein a segment of vein (e.g., a segment of a saphenous vein) is transected at two locations, any venous valves between those two locations are disrupted and the ends of the segment are then anastomosed into the arterial system, allowing the vein to function as an effective arterial bypass while leaving it in situ.

Circumferentially distensible stents are typically made from metallic materials including stainless steels and nickel-titanium alloys. Other materials are described in the literature as well, including polymeric materials. It is anticipated that any material useful for making a circumferentially distensible stent will function for the method of the present invention, although some materials may be preferable for long term use because of greater biocompatibility.

It is believed that self-expanding stents are preferred for the method of the present invention. Stents of this type are described by, for example, U.S. Pat. No. 4,503,569 to Dotter and U.S. Pat. No. 4,655,771 to Wallsten. These stents are typically made of braided steel wire which circumferentially distends when relieved of a restraining force (e.g., a catheter tube) or of nickel-titanium wire which circumferentially distends on exposure to increased temperatures such as body temperatures. Alternatively, stents requiring circumferential distension by the application of a separate, radially outward directed force applied from within the lumen of the stent (e.g., a catheter balloon) may also be used for the method of the present invention. See, for example, U.S. Pat. No. 4,733,665 to Palmaz.

In that relatively little force is expected to be required to hold the leaflets of a venous valve in an open position, it is anticipated that a stent with relatively few wires of relatively small diameter will suffice. This reduces the amount of metal exposed within the lumen of the vein. Conversely, it may be desirable to use a multiplicity of wires for the stent whereby the open interstices between adjacent wires are much smaller. In this fashion the stent may also be useful for occluding tributary vessels as well as holding open the leaflets of venous valves. The use of a multiplicity of wires provides a high likelihood that one or more individual wires will lie across the opening of a tributary vessel. One or more wires across the opening of the tributary can be expected to accumulate thrombus and may result in occlusion of the tributary at its opening into the vein segment.

It is believed that a preferred stent would be of such a length that would allow it to extend for the entire length of the vein segment. The stent in extending for the entire length of the vein segment (or at least a substantial portion thereof) would hold open the leaflets of all venous valves within the segment. Such a stent may be preferably designed to allow it to be cut to a desired length prior to implantation. As the typical length of saphenous vein used for in situ procedures can be expected to include 5-12 venous valves, the implantation of a single stent to hold open all valves is much more easily accomplished than is the location of all valves individually followed by implantation of an individual stent at each valve.

The stent should also have a circumferential distension range adequate to allow it to contact the lumen of the vein over the diametrical range of the vein segment between its proximal and distal ends. It should be of adequately small diameter in its collapsed state (i.e., prior to circumferential distension) to enable it to be inserted into the vein segment at the distal end whereby it can easily be inserted through the leaflets of all venous valves encountered within the vein segment.

Figure 9B:
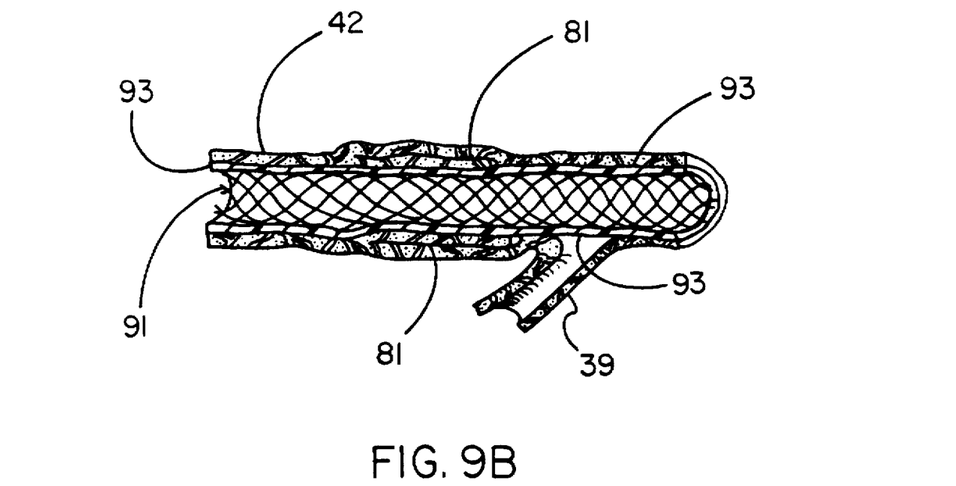
FIG. 9B describes the use of a covered stent to additionally occlude a tributary vessel.

Optionally, the stent may be provided with a thin covering of graft material if desired for certain applications. Such a covered stent is described by, for example, published PCT Patent Application WO 95/05132. The use of a covered stent allows for the reliable occlusion of tributary vessels, as well as holding open venous valves. FIG. 9B describes a longitudinal cross section showing a stent 91 provided with a covering 93 wherein the covered stent 91,93 is used to hold open the leaflets 81 of a venous valve and to occlude a side tributary 39 as well.

Various embodiments of the interior liner of the present invention are illustrated by the following examples which describe the construction, mechanical evaluation, implantation and in vivo evaluation of the liner. Example 1 describes the manufacture of an interior liner according to the above described procedure. Various alternative methods are also possible depending on the desired functional attributes of the interior liner. Many of these alternative methods are described in the various examples following Example 1. The porous PTFE film and the longitudinally extruded and expanded porous PTFE tube of all the following examples were all fabricated using CD123 fine powder PTFE resin (ICI America, Bayonne, N.J.) and following the teachings of U.S. Pat. Nos. 3,953,566 and 4,187,390.

EXAMPLE 1

This example describes an interior liner of the present invention useful primarily as a liner for blood conduits. It was made to require distension by a balloon catheter, to have a second circumference and to have minimal recoil. Having helically-wrapped layers of porous PTFE film applied in opposing directions, it is described in appearance by FIG. 2. It was manufactured according to the procedure described by the flow chart of FIG. 4.

To make this particular interior liner, a 3 mm inside diameter, longitudinally extruded and expanded porous PTFE tube was obtained. This tube had a wall thickness of about 0.25 mm and a fibril length of about 25 microns. The tube was fitted coaxially onto a 3 mm diameter stainless steel mandrel as described by step 1 of FIG. 4.

Next, a length of porous PTFE film was obtained that had been cut to a width of 5.1 cm. This film had a thickness of about 0.02 mm, a density of 0.2 g/cc and a fibril length of about 70 microns. Thickness was measured using a Mitutoyo snap gauge model No. 2804-10 and bulk density was calculated based on dimensions and mass of a film sample for comparison. Density of non-porous PTFE is considered to be 2.2 g/cc.

The fibril length of porous PTFE films used to construct the examples was estimated from scanning electron photomicrographs of an exterior surface of samples of the films. The fibril length of the longitudinally extruded and expanded porous PTFE tubes was determined to be the average of ten measurements between nodes connected by fibrils in the predominant direction of the fibrils. Ten measurements are made in the following manner. First, a micrograph is made of a representative portion of the sample surface, of adequate magnification to show at least five sequential fibrils within the length of the micrograph. Two series of five measurements are taken along a straight line parallel to the direction of orientation of the fibrils. A measurement constitutes the distance between adjacent nodes connected by fibril(s). The ten measurements obtained by this method are averaged to obtain the fibril length of the material. A total of ten measurements are taken without including fibril lengths of five microns or less.

Per step 2, this film was helically wrapped directly onto the bare metal surface of a 12 mm diameter stainless steel mandrel at an angle of 71 degrees with respect to the longitudinal axis of the mandrel so that three overlapping layers of film covered the mandrel; following this another three layers of the same film were helically wrapped over the first three layers with the second three layers applied at the same bias angle with respect to the longitudinal axis but in the opposite direction. The second three layers therefore were also oriented at an angle of 71 degrees with respect to the longitudinal axis but measured from the opposite end of the axis in comparison to the first three layers, so that the first and second layers were separated by an included angle of 38 degrees. According to step 3 the film-wrapped mandrel was then placed into a convection air oven set at 380° C. for 12 minutes to heat-bond the adjacent layers of film, then removed and allowed to cool. The resulting 12 mm inside diameter tube formed from the helically wrapped layers of film was then removed from the mandrel as described by step 4.

The 12 mm inside diameter porous PTFE film tube was then fitted coaxially over the 3 mm inside diameter, longitudinally extruded and expanded porous PTFE tube and mandrel, according to step 5. The film tube was then stretched longitudinally to cause it to reduce in diameter to the extent that it fit snugly over the outer surface of the 3 mm tube. The ends of this composite tube were then secured to the mandrel in order to prevent longitudinal shrinkage during heating. Per step 6 the combined tube and mandrel assembly was placed into an air convection oven set at 380° C. for 10 minutes to heat bond the film to the outer surface of the tube. The composite tube and mandrel assembly was then removed from the oven and allowed to cool.

According to steps 7 and 8 the film-covered porous PTFE tube was then removed from the 3 mm diameter mandrel and stretched to fit over an 8 mm diameter mandrel.

The tube and mandrel were then placed into an air convection oven set at 380° C. for two minutes per step 9, removed from the oven and allowed to cool (this heating step resulted in the final article having minimal recoil following release of a circumferentially distending force, as long as the liner is not forcibly distended beyond its 8 mm circumference). The composite tube was then removed from the 8 mm mandrel, according to step 10. As described by step 11, the composite tube was placed on a 3.2 mm mandrel and tension was applied to the opposite ends of the tube adequate to cause a reduction in the inside diameter of the liner to cause it to fit snugly on the mandrel. This was accomplished using a model no. 4201 Instron machine with flat face grips set at a crosshead speed of 200 mm/min. The Instron machine indicated that about 8 kg force was required to achieve the 3.2 mm liner inside diameter. This 3.2 mm inside diameter represents the initial inside diameter of the interior liner as a finished article available for use. The use of the 3.2 mm mandrel is not necessary; for ease, it may be preferable to tension the tube without using the mandrel.

An additional heat treatment was performed according to step 12 in order to dimensionally stabilize the tube to minimize any tendency for the tube to shrink longitudinally and increase in diameter if subjected to heat sterilization such as exposure to steam at 121° C. for 30 minutes. This was accomplished by placing the tube onto a 3.2 mm diameter stainless steel mandrel, applying a small amount of tension to the tube ends to ensure that the tube conformed uniformly to the surface of the mandrel, securing the tube ends to the mandrel to prevent longitudinal shrinkage, and placing the tube and mandrel into an air convection oven set at 200° C. for 20 minutes. After removal from the oven, cooling and removal of the tube from the mandrel per step 13, the resulting interior liner having an initial inside diameter of 3.2 mm was ready for sterilization and implantation into a blood conduit.

An interior liner made according to this description was subjected to steam sterilization at 121° C. for 30 minutes. The wall thickness of the sterilized liner was determined to be 0.25 mm while the inside diameter was determined to be 4.3 mm using a tapered, smooth-finished, graduated stainless steel mandrel.

Percentage recoil for the steam sterilized liner was determined by the previously described method to be 5.3 percent.

EXAMPLE 2

This example also appears as described by FIG. 2 and was made with the same process and materials as that of Example 1, except for the following differences. The 3 mm inside diameter, longitudinally extruded and expanded tube of 0.25 mm wall thickness described by step 1, was replaced with an otherwise identical tube having a 0.10 mm wall thickness and a 30 micron fibril length. The porous PTFE film of step 2 was of 2.5 cm width rather than the 5.1 cm width. Likewise the mandrel about which the film was helically wrapped in step 2 was of 10 mm diameter rather than 12 mm diameter. The heat treatment described by step 3 was performed at 380° C. for 11 minutes rather than 12 minutes. In step 8 the larger mandrel used was of 10 mm rather than 8 mm diameter. Finally, in step 11, only about 5 kg of force was required to tension the tube to cause it to conform to the 3.2 mm diameter mandrel. The resulting interior liner was distensible at normal human blood pressures and consequently did not require the greater pressure of a balloon for distension.

An interior liner made according to this description was subjected to steam sterilization at 121° C. for 30 minutes. The wall thickness of the sterilized liner was determined to be 0.12 mm while the inside diameter was determined to be 4.1 mm using a tapered, smooth-finished, graduated stainless steel mandrel.

Percentage recoil for the steam sterilized liner was determined by the previously described method to be 1.1 percent.

Three samples were subjected to increasing internal pressure in increments of 5 psi (35 KPa) via water-filled latex bladders at room temperature. All samples burst at approximately 10 mm outer diameter. These results confirm the presence of the second circumference.

Figure 4:
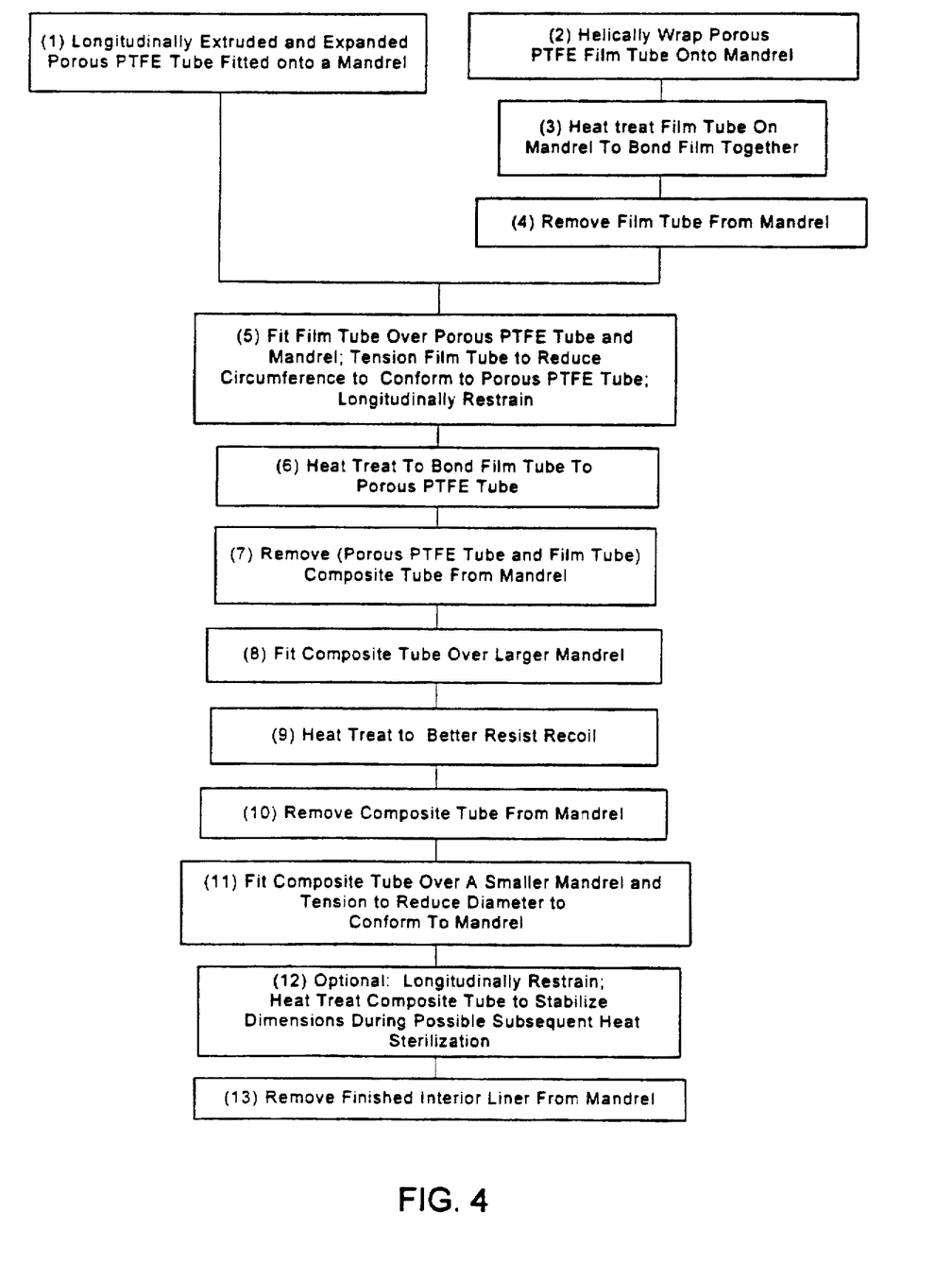
FIG. 4 shows a flow chart that describes a process for making a preferred interior liner of the present invention.

This Example constitutes a preferred embodiment due to the blood pressure distensibility, minimal recoil, and the fact that the mandrel diameters of steps 2 and 8 of FIG. 4 are the same.

EXAMPLE 3

An example was made which was circumferentially distensible up to a second circumference; however, process step 9 intended to better resist recoil following the release of the distending force was omitted. The physical appearance of this example is also described by FIG. 2.

This example was made from the same materials and by the same method as Example 1 with the omission of step 9 of FIG. 4. The film-covered porous PTFE tube of step 8 was removed from the 8 mm diameter mandrel per step 10, after which about 8 kg tension was applied to the ends of the tube adequate to cause the tube to assume the 3.2 mm diameter of the mandrel according to step 11.

An interior liner made according to this description was subjected to heat sterilization in an air convection oven at about 145° C. for 15 minutes. Steam was not used. The inside diameter was determined to be 3.7 mm using a tapered, smooth-finished, graduated stainless steel mandrel.

Percentage recoil for the heat sterilized liner was determined by the previously described method to be 11.3 percent, in contrast to the liner of Example 1 which exhibited 5.3 percent recoil.

For comparison, percentage recoil for a commercially available vascular graft of the prior art was evaluated. The particular graft considered, an Impra Graft 3 mm thin wall (Impra product code 10S03TW, Impra, Inc. Tempe, Ariz.) did not incorporate an exterior helical wrapping of porous PTFE film and was considered to be circumferentially distensible. This graft was readily distended by 25 percent as required by the percentage recoil determination method described above. The percentage recoil for this graft was 15.4 percent, in contrast to the liner of Example 1 which exhibited 5.3 percent recoil.

EXAMPLE 4

An interior liner was made as shown by FIG. 1 to be circumferentially distensible by blood pressure. To construct this example a 5 mm inside diameter longitudinally extruded and expanded porous PTFE tube was obtained. The tube had a wall thickness of about 0.05 mm and a fibril length of about 25 microns. The tube was fitted coaxially over a 5 mm stainless steel mandrel, after which a helical wrapping of 1.9 cm wide porous PTFE film of the same type used to construct Example 1 was applied over the outer surface of the 5 mm inside diameter porous PTFE tube using a wrap angle of 23° with respect to the longitudinal axis of the mandrel. This helical wrapping of film was applied in one direction only. The tube and mandrel were then placed into an air convection oven set at 380° C. for 6.5 minutes to heat bond the film to the outer surface of the tube. The tube and mandrel were then removed from the oven and allowed to cool, after which the tube was removed from the 5 mm diameter mandrel and carefully fitted over a 7 mm mandrel. The tube was then removed from the 7 mm mandrel and tension was applied to the ends of the tube adequate to cause the tube to assume its previous approximate 5 mm inside diameter.

Internal pressure was applied to the liner via a water-filled latex bladder. The water pressure was steadily increased to about 60 psi (415 KPa), at which pressure the tube ruptured. It was noted that this tube exhibited a tendency to twist along its longitudinal axis with increasing pressure. It is believed that this resulted from the application of the helically-wrapped film in a single direction rather than in opposite directions along the longitudinal axis. This twisting behavior was unique to this example.

EXAMPLE 5

This example describes an interior liner made so as not to have a second circumference. The liner of this example is circumferentially distensible by balloon catheter and has minimal recoil. It is different in construction from Example 1 in that no porous PTFE film is used to cover the outer surface of the longitudinally extruded and expanded porous PTFE tube; its physical appearance is described by the longitudinally extruded and expanded tube 12 portion of FIG. 1. Embodiments of the interior liner of this type may be preferred for various peripheral vascular applications wherein it is desired to provide an interior lining for living vessels and particularly advantageous for the lining to exhibit minimal recoil.

This example was made by first obtaining a 3 mm inside diameter, longitudinally extruded and expanded tube, carefully fitting it over an 8 mm diameter stainless steel mandrel. The tube and mandrel were placed into an air convection oven set at 380° C. for two minutes, removed and allowed to cool to about room temperature. A 3 mm diameter stainless steel mandrel was inserted into the tube and 8 kg tension was applied to the tube ends extending beyond the ends of the mandrel to cause the tube to reduce in diameter to the extent that the inner surface of the tube conformed smoothly and uniformly to the outer surface of the mandrel. The ends of the tube were secured to the mandrel to prevent longitudinal shrinkage and the tube and mandrel were placed into an air convection oven set at 200° C. for twenty minutes, removed and allowed to cool. This final heat treatment was performed to keep the porous PTFE tube dimensionally stable during steam sterilization.

An interior liner made according to this description was subjected to a heat sterilization in an air convection oven at about 145° C. for 15 minutes. Steam was not used. The inside diameter was determined to be 3.6 mm using a tapered, smooth-finished, graduated stainless steel mandrel.

Percentage recoil for the heat sterilized liner was determined by the previously described method to be 5.7 percent.

EXAMPLE 6

An interior liner was made using layers of helically-wrapped film applied directly to the surface of a stainless steel mandrel so that the liner did not incorporate a substrate tube of longitudinally extruded and expanded porous PTFE. This liner was made as described by steps 2, 3 and 4 of FIG. 4. A 2.5 cm wide film was applied to 10 mm diameter stainless steel mandrel and subsequently heat treated at 380° C. for 11 minutes. After cooling and removal from the mandrel the liner was tensioned using a force of about 1 kg which resulted in a reduction in inside diameter from about 10 mm to about 1 mm. The circumferential distensibility of the resulting film tube was evaluated by inserting a latex bladder into the film tube and pressurizing the bladder with water at about room temperature. One end of the film tube and bladder were secured to a pressure supply fitting; the opposite end of the film tube was secured to the closed end of the bladder. The diameter of the film tube increased steadily as the pressure increased until a pressure of 25 psi (170 KPa) was achieved at which pressure the film tube diameter was about 8.2 mm. The diameter increased only slightly with further increasing pressure, reaching 9.4 mm at a pressure of about 40 psi (275 KPa). The film tube ruptured before 45 psi (310 KPa) was achieved.

In addition to demonstrating the circumferentially distensible character and the second circumference of the film tube, this evaluation also demonstrated the practical potential of the liner as an exterior covering capable of reinforcing other conduits. The effectiveness of the film tube as an external covering was made apparent by inflating another sample of the latex bladder material without the external covering with water at about room temperature; a pressure of 10 psi (70 KPa) resulted in a bladder diameter of 19.2 mm.

EXAMPLE 7

Figure 7A:
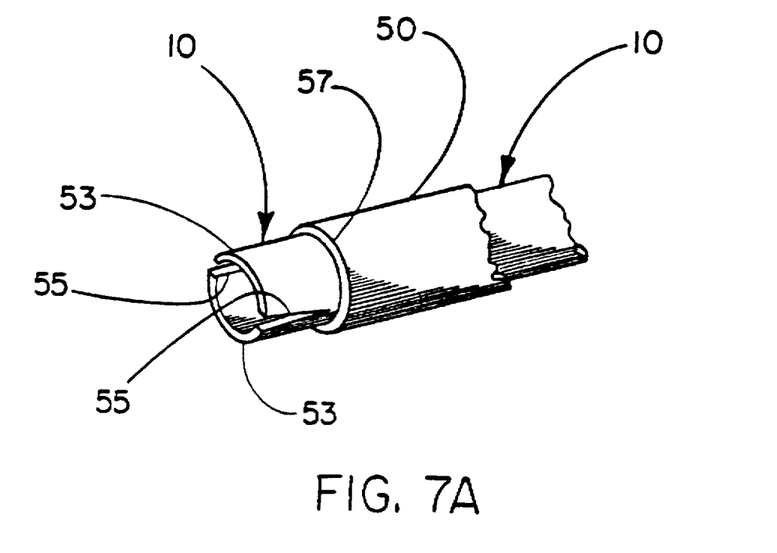
FIGS. 7A and 7B describe a method of anastomosing the interior liner to a blood conduit using sutures.
Figure 7B:
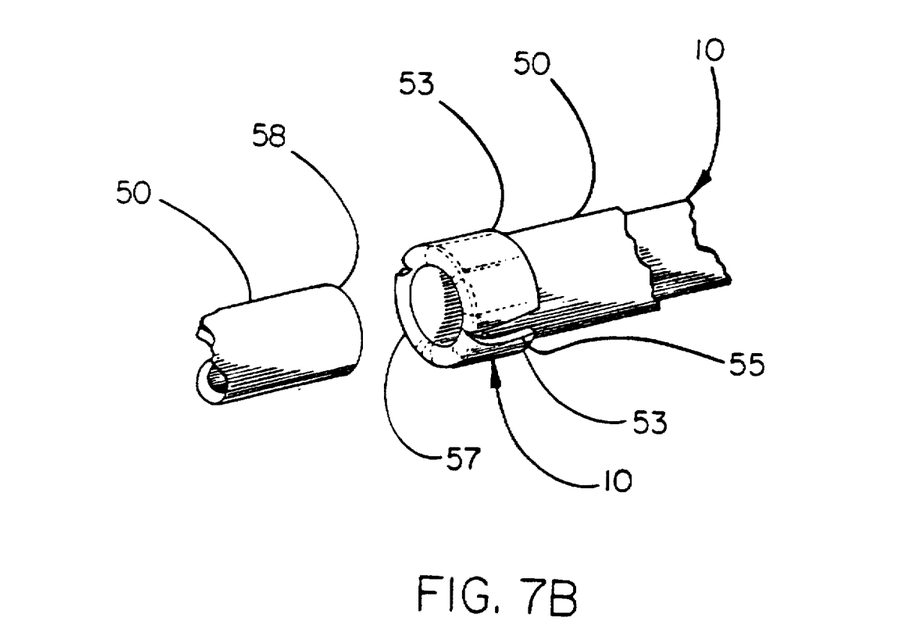

In a study using a 29 kg adult female greyhound dog, a 6 mm DIASTAT® Vascular Access Graft with a 15 cm long cannulation segment was implanted into the right leg in a looped femoral artery to femoral vein shunt configuration. Two weeks after this implantation, an interior liner made as described by Example 1 was placed into the DIASTAT Vascular Access Graft in the right leg after the liner had been steam sterilized at 121° C. for 30 minutes. Partial transverse graftotomies were completed at both arterial and venous limbs of the graft. The graftotomies allowed a 40 cm long 5F embolectomy catheter access into the graft lumen to be used to position the interior liner within the vascular graft. Alternatively a plastic-coated cable having a bullet-shaped tip to which the liner can be temporarily secured may be used to pull the liner into position within the graft. The interior liner was axially positioned such that the liner was longer than the graft section to be lined and extended beyond both ends of the graft segment. A Schneider Match 35® Percutaneous Transluminal Angioplasty catheter (Schneider, Minneapolis, Minn.) was inserted into the interior liner at the venous graftotomy such that the tip of the balloon protruded through the arterial graftotomy. The catheter had an inflated balloon diameter of 7 mm and a length of 4 cm. The balloon was pressurized to approximately 8 atmospheres, thus increasing the circumference of the interior liner and causing it to conform to the luminal surface of the 6 mm DIASTAT Vascular Access Graft. The balloon was then moved approximately 2 cm down the length of the interior liner toward the venous graftotomy. As shown by FIGS. 7A and 7B, two longitudinal cuts 55 approximately 180° apart were made into the end 53 of the interior liner 10, thus bisecting the circular cross-section into two semi-circles. The end 53 of the liner 10 was then everted over the end 57 of the 6 mm DIASTAT Vascular Graft 50, and the two ends 57 and 58 of the vascular graft 50 (one of which incorporated the interior liner) were then reconnected in an end-to-end fashion using a suture (not shown). A single CV7 GORE-TEX® Suture with TT9 needles was used. Once the arterial anastomosis was completed, the balloon was moved toward the venous graftotomy in approximately 2 cm increments and inflated, thus causing the entire length of the liner to conform to the lumen of the DIASTAT® Vascular Access Graft. Next the balloon was removed and the venous anastomosis was completed in the same manner as the arterial anastomosis. The completion of both the arterial and venous anastomoses resulted in the lining of an 18 cm segment (centered about the cannulation segment) of the 6 mm DIASTAT Vascular Access Graft. With the liner installed, the clamps were released, reestablishing flow. An angiograph was then taken of the graft incorporating the interior liner. Once blood flow was re-established in the 6 mm DIASTAT Vascular Access Graft having the liner, a 6 mm DIASTAT Vascular Access Graft with a 15 cm cannulation segment was implanted in a looped femoral artery to femoral vein shunt configuration in the left leg as a contralateral control graft. Both the lined and the unlined grafts remained in life for an additional two weeks.

At the end of this two week period the DIASTAT Vascular Access Graft incorporating the interior liner was angiographed. After taking the angiograph, the vascular graft and interior liner were cannulated by two 15 gauge dialysis needles, one in the arterial, and one in the venous limb of the shunt. Digital pressure was held over each puncture site for five minutes which resulted in hemostasis. This procedure was then repeated until a total of four punctures were present through the graft. With the cannulation completed, angiographs were taken of both the lined and unlined grafts and the samples were explanted.

On the contralateral control graft, 10 minutes was required to reach hemostasis for each of the four cannulation sites.

Comparison of the angiographs taken before and after lining the DIASTAT Vascular Access Graft showed good blood flow as a result of placing the lining into the vascular graft. The same findings were obtained from angiographs made before and after cannulation of the lined graft. Evaluation of the explanted DIASTAT Vascular Access Grafts revealed that the grafts were well attached to the surrounding tissue. The interior liner appeared well adhered and conformed to the inner surface of the surrounding graft, particularly at the cannulation sites, where there was no evidence of separation between the interior liner and the 6 mm DIASTAT Vascular Access Graft. The flow surface of the liner was wrinkle-free, clean and free of thrombus. The contralateral control graft was also clean and free of thrombus.

EXAMPLE 8

Another animal study was performed to evaluate the interior liner in use as a liner for a living blood vessel. The venous anastomosis of an arteriovenous vascular graft was lined thereby providing the venous end of the graft, the venous anastomosis and the adjacent vein a new, continuous luminal surface covering. An application of this type would provide an indication of the effectiveness of the interior liner as a treatment for venous stenosis. Accordingly, 6 mm GORE-TEX® Stretch Vascular Grafts were installed in loop arteriovenous shunt configurations in each leg of a 27.1 kg adult greyhound dog in a similar manner as previously described, except that the loops were not completed with both anastomoses next to each other. Rather, the venous anastomosis was located further down the length of the leg, approximately midway between the hip and the knee. Configuring the loop as such placed the venous anastomosis within a segment of the femoral vein which was approximately 6 mm in diameter. The segment of the femoral vein approximately 2 to 3 cm proximal from the venous anastomosis, which was intended to be provided with an interior liner, ranged from approximately 6 to 8 mm in diameter.

With the 6 mm GORE-TEX Stretch Vascular Grafts installed and blood flow initiated, further dissection was completed, exposing more of the host vein proximal to the venous anastomosis. This was done so that any branches connecting into the femoral vein could be ligated. In addition, the femoral vein distal to the venous anastomosis was ligated (it is believed that distal vein ligation may not be necessary). At this point, the 6 mm GORE-TEX Stretch Vascular Graft was the only conduit providing flow to the femoral vein within the surgically exposed region.

Once the diameter of the left femoral vein downstream from the venous anastomosis was assessed, blood flow through the section to be provided with the interior liner was stopped by clamping. A complete transverse graftotomy was completed approximately 3 cm upstream of the venous anastomosis, through which the liner was introduced. The liner extended 2 to 3 cm into the living vein. The liner was then deployed, and the end located in the vascular graft was attached as previously described. The distal end of the interior liner was not mechanically attached to the vein in any fashion.

The venous anastomosis in the left leg of the animal was provided with an interior liner of the same type and dimensions as described in Example 1. A 7 mm angioplasty balloon inflated to 8 atmospheres was used to increase the circumference of the liner as necessary to conform to the venous anastomosis and adjacent vein and GORE-TEX Stretch Vascular Graft.

After the interior liner had been deployed in the left leg of the animal using the balloon catheter, blood flow was reestablished by the release of the proximal and then the distal clamp. The interior liner was again visible without wrinkles through the wall of the vein. It was noted that occasionally the vein dilated around the liner, allowing blood to reside between the two. The vein eventually became stabilized in the region provided with the interior liner. Flow through the liner was allowed to continue for 21 minutes. Upon explant, no wrinkles were detected, and the luminal surface of the interior liner appeared clean and free of any clot.

The venous anastomosis in the right leg of the animal was provided with an interior liner made in accordance with process described in the flow chart of FIG. 4. According to step 1 a longitudinally extruded and expanded 3 mm porous PTFE tube having a 30 micron fibril length and a 0.10 mm wall thickness was fitted over a 3 mm mandrel. Per step 2 a 5 cm wide porous PTFE film of the same type as described previously was helically wrapped as described previously around a 12 mm diameter mandrel. The mandrel and film tube were heated according to step 3 at 380° C. for 12 minutes and subsequently the combined tubes were heated as described by step 6 at 380° C. for 10 minutes. The composite tube was fitted over a 10 mm mandrel as described by step 8 and heated at 380° C. for 2 minutes as described by step 9. For step 11, a 3.2 mm diameter mandrel was used with about 5 kg of tension applied to the tube. The heat treatment of step 12 was accomplished at 200° C. for 20 minutes. Finally, the resulting liner was heat sterilized at 145° C. for 15 minutes without the use of steam. This liner was fitted into position in a similar manner as described previously except that a balloon catheter was not used for deployment. Instead, following anastomosis of the proximal end of the interior liner, the blood pressure of the animal was used to supply the force necessary to increase the circumference to cause the liner to conform to the inside surface of the venous anastomosis of the vein and the 6 mm GORE-TEX Stretch Vascular Graft and adjacent segments of each.

After the deployment of this 0.10 mm thick interior liner at the venous anastomosis in the right leg of the dog, it was observed that the restored blood flow caused the interior liner to quickly increase in circumference, smoothly conforming to the region of the venous anastomosis. The interior liner was readily visible through the femoral vein, and it was clear that no wrinkles were present. Occasionally, due to the deep breathing of the dog causing an increase in thoracic pressure, the vein surrounding the liner dilated more than the interior liner, allowing blood to reside in the resulting coaxial space. The resident blood, however, evacuated quickly when the thoracic pressure decreased, and the vein returned to the same diameter as the interior liner. As time went on, the vein ceased to dilate in the area which was lined. The cessation of this behavior first occurred near the vein-graft anastomosis, then with time, larger and larger areas of the lined vessel became stabilized. Flow through the liner was allowed to continue for 82 minutes. Upon explant, no wrinkles were detected, and the luminal surface of the liner appeared clean and free of any clot.

EXAMPLE 9

A cryo-preserved human saphenous vein was obtained; the vein was of about 30 cm length and had inside diameters of about 6 mm at the proximal end and 4 mm at the distal end. The vein was placed in a basin with the proximal end occluded by a hemostat; an irrigation sheath was inserted into the distal end. Saline solution was introduced into the vein via the irrigation sheath at a pressure approximately equal to human physiological blood pressure (about 100–125 mm Hg); flow of the saline solution through the vein tributaries was observed. The lumen of the vein was angioscopically examined and the location of two intact venous valves within the vein was noted. An intraluminal graft as described by Example 2 was inserted into the full length of the vein. Insertion was accomplished by first ligating one end of the intraluminal graft with a suture, placing the intraluminal graft on a GORE Eze-Sit™ Valvulotome Catheter (W. L. Gore and Associates, Inc., Flagstaff Ariz.) with the Blunt Introducing Head installed and introducing it into the vein in a distal-to-proximal direction while the vein was pressurized with the saline solution. The catheter was then withdrawn; the hemostat was removed from the vein and re-clamped over both the vein and the intraluminal graft, again at the proximal end.

The intraluminal graft was next infused distally with saline solution at the same pressure used previously. The graft distended quickly and easily along with the vein, within about three seconds. No flow was observed from any of the tributaries at this time; all of the tributaries appeared to be completely occluded by the intraluminal graft.

The lumen of the graft was then angioscopically inspected in order to observe the state of the venous valves. Both valves appeared to be held fully open to the extent that their locations were quite difficult to locate by visualization from within the intraluminal graft lining the vein.

While the principles of the invention have been made clear in the illustrative embodiments set forth above, it will be obvious to those skilled in the art to make various modifications to the structure, arrangement, proportion, elements, materials and components used in the practice of the invention. To the extent that these various modifications do not depart from the spirit and scope of the appended claims, they are intended to be encompassed herein.

We claim:

1. A method of performing an in situ bypass, comprising:
   a. creating a vein segment;
   b. inserting a circumferentially distensible intraluminal graft into the vein segment and into at least one venous valve within the vein segment;
   c. circumferentially distending the intraluminal graft, thereby holding open the at least one venous valve; and
   d. anastomosing the vein segment to adjacent arteries.
2. A method according to claim 1 wherein the intraluminal graft also occludes at least one tributary to the vein.
3. A method according to claim 1 wherein the intraluminal graft holds open at least two venous valves.
4. A method according to claim 1 wherein the intraluminal graft is comprised of porous PTFE.
5. A method according to claim 4 wherein the intraluminal graft has a first circumference prior to distension and wherein the intraluminal graft has a second, larger circumference resulting from distension by the application of internal pressure.
6. A method according to claim 4 wherein the intraluminal graft has a wall thickness of less than about 0.25 mm.
7. A method according to claim 6 wherein the intraluminal graft has a wall thickness of less than about 0.10 mm.
8. A method according to claim 5 wherein the intraluminal graft has a wall thickness of less than about 0.25 mm.
9. A method according to claim 8 wherein the intraluminal graft has a wall thickness of less than about 0.10 mm.
10. A method according to claim 5 wherein the intraluminal graft exhibits minimal recoil of 14 percent or less.
11. A method according to claim 10 wherein the intraluminal graft exhibits minimal recoil of 10 percent or less.
12. A method according to claim 11 wherein the intraluminal graft exhibits minimal recoil of 7 percent or less.
13. A method according to claim 5 wherein the porous PTFE intraluminal graft comprises an inner layer having a microstructure with axially oriented fibrils and at least one outer layer having a microstructure with helically oriented fibrils.
14. A method according to claim 5 wherein the internal pressure is the result of the use of a liquid.
15. A method according to claim 14 wherein the liquid is chosen from the group consisting of water, saline and blood.
16. A method according to claim 2 wherein the intraluminal graft holds open leaflets of at least two venous valves.
17. A method according to claim 2 wherein the intraluminal graft is comprised of porous PTFE.
18. A method according to claim 17 wherein the intraluminal graft has a first circumference prior to distension and wherein the intraluminal graft has a second, larger circumference resulting from distension by the application of internal pressure.
19. A method according to claim 17 wherein the intraluminal graft has a wall thickness of less than about 0.25 mm.
20. A method according to claim 19 wherein the intraluminal graft has a wall thickness of less than about 0.10 mm.
21. A method according to claim 18 wherein the intraluminal graft has a wall thickness of less than about 0.25 mm.
22. A method according to claim 21 wherein the intraluminal graft has a wall thickness of less than about 0.10 mm.
23. A method according to claim 5 wherein the intraluminal graft has first and second opposing ends and wherein the second circumference at the first opposing end is larger than the second circumference at the second opposing end.
24. A method of holding leaflets of a venous valve in an open condition, comprising inserting a circumferentially distensible tubular article into a segment of a vein and into a venous valve within the vein, and circumferentially distending the tubular article, thereby holding open the leaflets of the venous valve.
25. A method according to claim 24 wherein the segment of a vein has a length and the tubular article extends for the length of the segment of the vein.
26. A method according to claim 24 wherein the tubular article is an intraluminal graft.
27. A method according to claim 26 wherein the intraluminal graft is comprised of porous PTFE.
28. A method according to claim 24 wherein the tubular article is a stent.
29. A method according to claim 28 wherein the stent is provided with a covering of graft material.

* * * * *